(12) United States Patent
Johnson

(10) Patent No.: US 8,084,731 B2
(45) Date of Patent: Dec. 27, 2011

(54) SENSOR SYSTEM FOR LIQUID DETECTION WITH LENS COMPONENT HAVING AN APEX

(76) Inventor: Douglas M. Johnson, Seattle, WA (US)

( * ) Notice: Subject to any disclaimer, the term of this patent is extended or adjusted under 35 U.S.C. 154(b) by 749 days.

(21) Appl. No.: 11/852,233

(22) Filed: Sep. 7, 2007

(65) Prior Publication Data
US 2008/0078924 A1 Apr. 3, 2008

Related U.S. Application Data

(60) Provisional application No. 60/843,515, filed on Sep. 9, 2006.

(51) Int. Cl.
*G02B 6/42* (2006.01)

(52) U.S. Cl. ............... 250/227.25; 250/208.2; 250/239; 250/216; 257/434

(58) Field of Classification Search ............ 250/208.2, 250/216, 214.1, 214 R, 239, 227.11, 227.25, 250/227.2; 257/431, 432, 433, 434, 678, 788

See application file for complete search history.

(56) References Cited

U.S. PATENT DOCUMENTS

| 5,247,167 A * | 9/1993 | Bargerhuff et al. ........ 250/208.1 |
| 5,712,934 A | 1/1998 | Johnson |
| 2004/0026757 A1 * | 2/2004 | Crane et al. .................. 257/434 |

* cited by examiner

*Primary Examiner* — Francis M Legasse, Jr.
(74) *Attorney, Agent, or Firm* — Christensen O'Connor Johnson Kindness PLLC

(57) ABSTRACT

A light transmitting optical fiber shines light at a side edge portion of a hemispherical lens. The light is transmitted along the outer periphery of the lens to a second side edge portion located opposite the first side edge portion. A light sensitive component detects light at the second edge portion which light originated at the first side edge portion. The intensity of light detected at the second side edge portion is indicative of the fluid to which the lens is exposed.

2 Claims, 15 Drawing Sheets

SENSOR SYSTEM FOR LIQUID DETECTION WITH LENS COMPONENT HAVING AN APEX

CROSS-REFERENCE TO RELATED APPLICATION

This application claims the benefit of U.S. Provisional Application No. 60/843,515, on filed Sep. 9, 2006.

BACKGROUND

U.S. Pat. No. 5,712,934, issued Jan. 27, 1998, describes a "Fiber Optic Infrared Sensor" to detect the presence of water (as compared to air) or another fluid having a refractive index substantially greater than air. Such system uses a return bent optical fiber. Light is transmitted into one end of the fiber, and a photosensitive component provides a measure of the intensity of light leaving the other end. As described in such patent, the intensity of light sensed at the output end provides an indication of the presence of water or another fluid at the bend of the fiber. This technology has been in use in the "EOS" (environmental optical sensor) product available from Cambria Corporation of Seattle, Wash. Other fiber optic sensing systems are described and cited in U.S. Pat. No. 5,712,934.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a novel, optical sensing system which, in one application, can be used to detect the presence of liquid (such as water, alcohol, petroleum products, or a mixture thereof) between the walls of a double-walled underground fuel tank. For example, if ground water seeps through the outer wall, it will be detected; and if a fuel product leaks through the inner wall, the fuel will be detected.

In one aspect of the invention, a sensor uses a generally hemispherical lens of optically translucent material formed integral with a flat annular peripheral flange. The lens-flange component is mounted in a depression (recess, socket, countersink) of a special holder. The holder is formed with precisely positioned holes for snugly receiving the end portions of two optical fibers, such that the flat ends of the fibers are centered along opposite sides of the curved lens.

In another aspect of the invention, an array of vertically spaced sensors is provided, each shielded from direct contact along a longitudinal direction of a housing for the sensors.

In another aspect of the invention, a special "detangler" is provided for receiving and holding the end portions of the optical fibers opposite the end portions adjacent to the lens (es). The detangler component is easily attachable to a mating connector of a circuit board having a microprocessor to provide power to light emitting components and detect intensity of light returning to photosensitive components.

In another aspect of the invention, a special "tamper" feature is incorporated at the distal end of the sensor housing to provide an indication of whether or not the housing has left a predetermined position.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6A is a diagram of the anti-tamper process.

DETAILED DESCRIPTION

Figure 1:
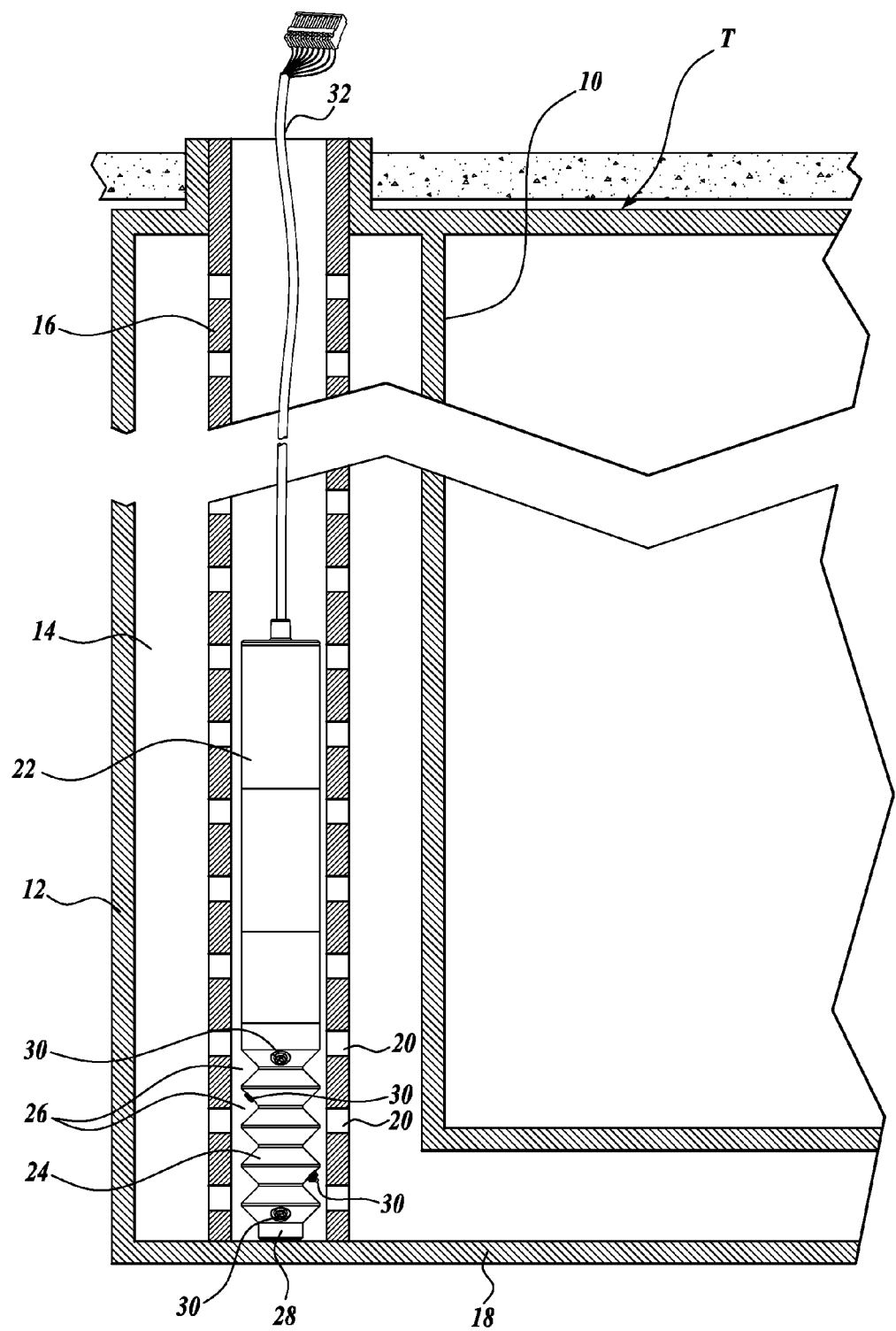
FIG. 1 (prior art) is a diagrammatic side elevation of a double-walled tank having a known sensor system for liquid detection, with parts shown in section.
Figure 2:
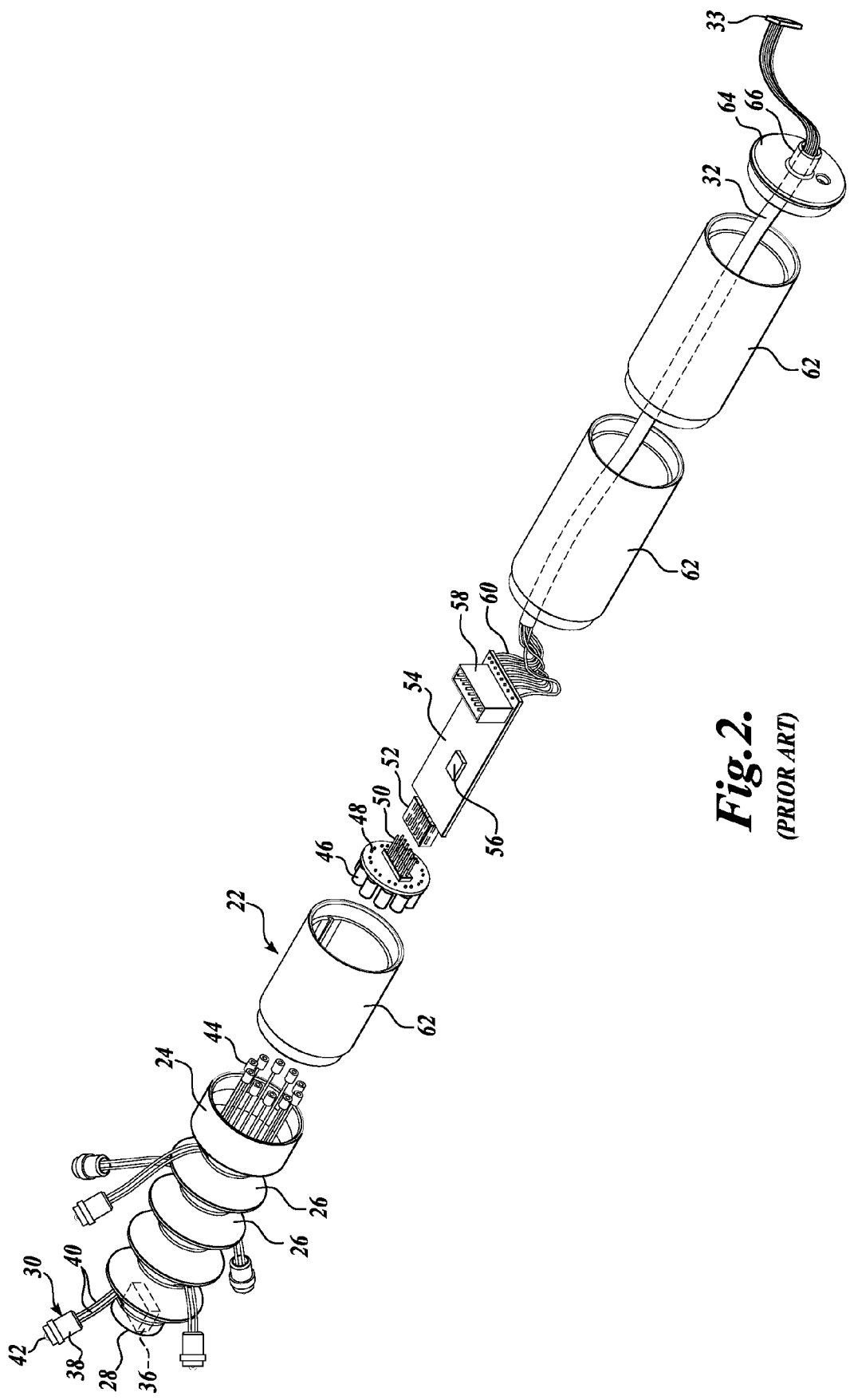
FIG. 2 (prior art) is a perspective of the sensor component of FIG. 1 with parts in exploded relationship.
Figure 3:
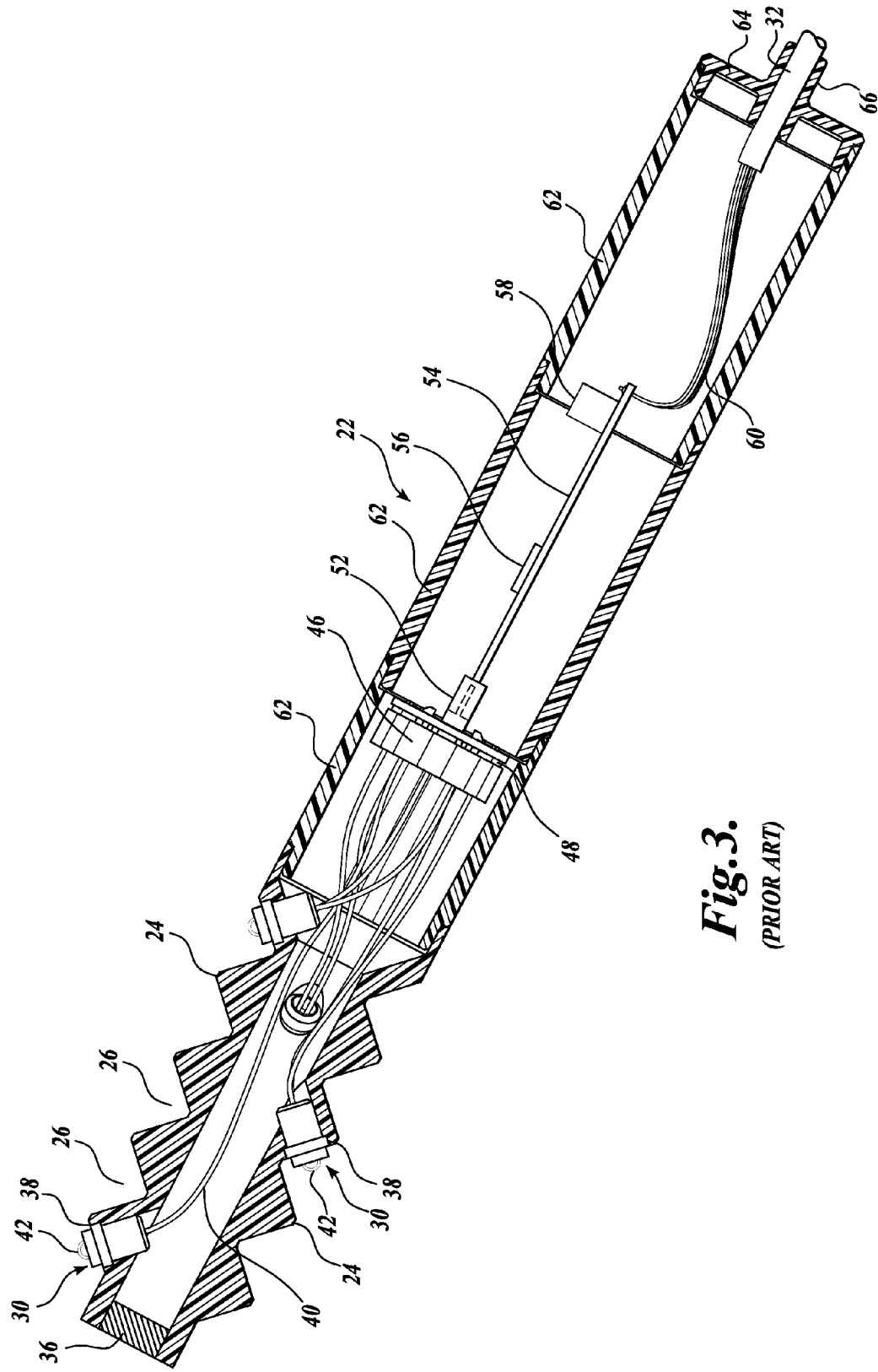
FIG. 3 (prior art) is a side elevation of the sensor component of FIG. 1 and FIG. 2 with parts assembled and parts shown in section.

The optical sensor system shown diagrammatically in FIGS. 1, 2, and 3 is a prior art system sold under the trademark "EOS" (environmental optical sensor) by Cambria Corporation of Seattle, Wash. Such sensor is based on the construction and principles described and cited in U.S. Pat. No. 5,712,934. As for the drawings of the present invention (FIGS. 4-18), the dimensions in FIGS. 1-3 are exaggerated for ease of illustration and description.

FIG. 1 illustrates an underground tank T having inner and outer walls 10, 12 with a vertical space 14 between them. In the known EOS system, a perforated mounting pipe 16 extends vertically through the space 14 from the metal bottom 18 of the outer tank to the top of the tank. Typically, only air is in the space 14 between the tank inner and outer walls. Perforations 20 (shown diagrammatically) of the upright mounting pipe 16 permit liquid to enter the pipe in case of a malfunction, such as entrance of water from the exterior of the tank or leakage of fuel from the interior.

The sensor system includes a cylindrical housing 22 somewhat loosely received in the pipe 16. The bottom or distal end portion 24 of the housing is shaped with vertically spaced V grooves 26 such that the distal end portion resembles a partially opened accordion fold, although it is rigid, such as a rigid plastic. A narrow foot 28 at the bottom rests on the metallic bottom 18 of the outer wall. Individual optical sensors 30 of the type described in U.S. Pat. No. 5,712,934 are spaced vertically along the distal end portion 24. An output cable 32 extends from the housing 22, upward and out of the tube 16 for connection to appropriate equipment for receiving the outputs from the sensor system.

Details of the prior art sensor construction are shown in more detail in FIGS. 2 and 3. The narrow sensor foot 28 can contain a magnet 36. Such magnet interacts with a reed switch mounted at the bottom of the mounting pipe to indicate that the sensor housing 22 is located at the bottom. Wires from the reed switch (not shown) extend upward along the sensor, to the top of the mounting pipe for an additional, position-indicating output.

The distal end portion of the housing is hollow, and the individual sensors 30 have cylindrical holders 38 that receive a length of optical fiber 40. One stretch of the fiber extends lengthwise through its holder to an exposed return bend 42 which leads to the other stretch of the fiber. The fiber ends have cylindrical sleeves 44 sized to fit in socketed protrusions 46 of a coupler 48. Such coupler has pins 50 to mate with a standard connector 52 from a printed circuit board 54 on which a microprocessor 56 is mounted. During assembly, programming access to the microprocessor is provided by way of a standard coupling 58. Output wires 60 extend to and through the output cable 32. The cable can terminate at a standard multipin connector 33.

The top or proximate end portion of the housing can include one or more innerfitting cylindrical shells 62 and a top or proximate end cap 64 with a hollow hub portion 66 through which the cable 32 extends. The shell(s) are designed to hold the circuit board stably in position and, after assembly, the interior can be filled with potting material.

The socketed protrusions 46 of the coupler 48 contain, alternately, a light source (such as a light emitting diode) and a photosensitive device (such as a photodiode). For each individual sensor 30, one length of its optical fiber 40 extends from a light source and, by total internal reflection, carries light to the respective bend 42. Depending on the medium to which the bend is exposed, light returns by way of the other length 40 of the fiber, which leads to the photosensitive component. The photosensitive component provides an indication of the intensity of light received. This information is analyzed by the microprocessor which indicates characteristics of the fluid to which the bend 42 of the sensor is exposed, by way of the output wires 60.

In general, and without repeating the detailed description from U.S. Pat. No. 5,712,934, highly efficient transmission of light by total internal reflection may be obtained in a length of optical fiber. Nevertheless, light losses may result from, for example, refractive loss resulting from incident light striking the fiber wall at less than the critical angle. Additional losses may be attributed to optical impurities present within the fiber, which may scatter or absorb light. In addition, the attenuation of light intensity through an optical fiber, particularly a bent fiber, may result from engagement with a medium having a refractive index substantially different than that of the fiber. In the system of U.S. Pat. No. 5,712,934, light loss at the return bend of the fiber is much greater for water than for air, and detectably different for gasoline than for either water or air. Many devices and methods, in addition to that of U.S. Pat. No. 5,712,934, take advantage of the attenuation of light intensity through a light-conducting medium as a consequence of engaging an optical component with a medium such as a liquid.

In the system of FIGS. 1, 2, and 3, wires 60 include a power input wire, a ground wire, and various output wires to indicate whether or not the sensors detect air, water, or gasoline. This provides an environmental safeguard for a defective or damaged fuel tank.

Figure 4:
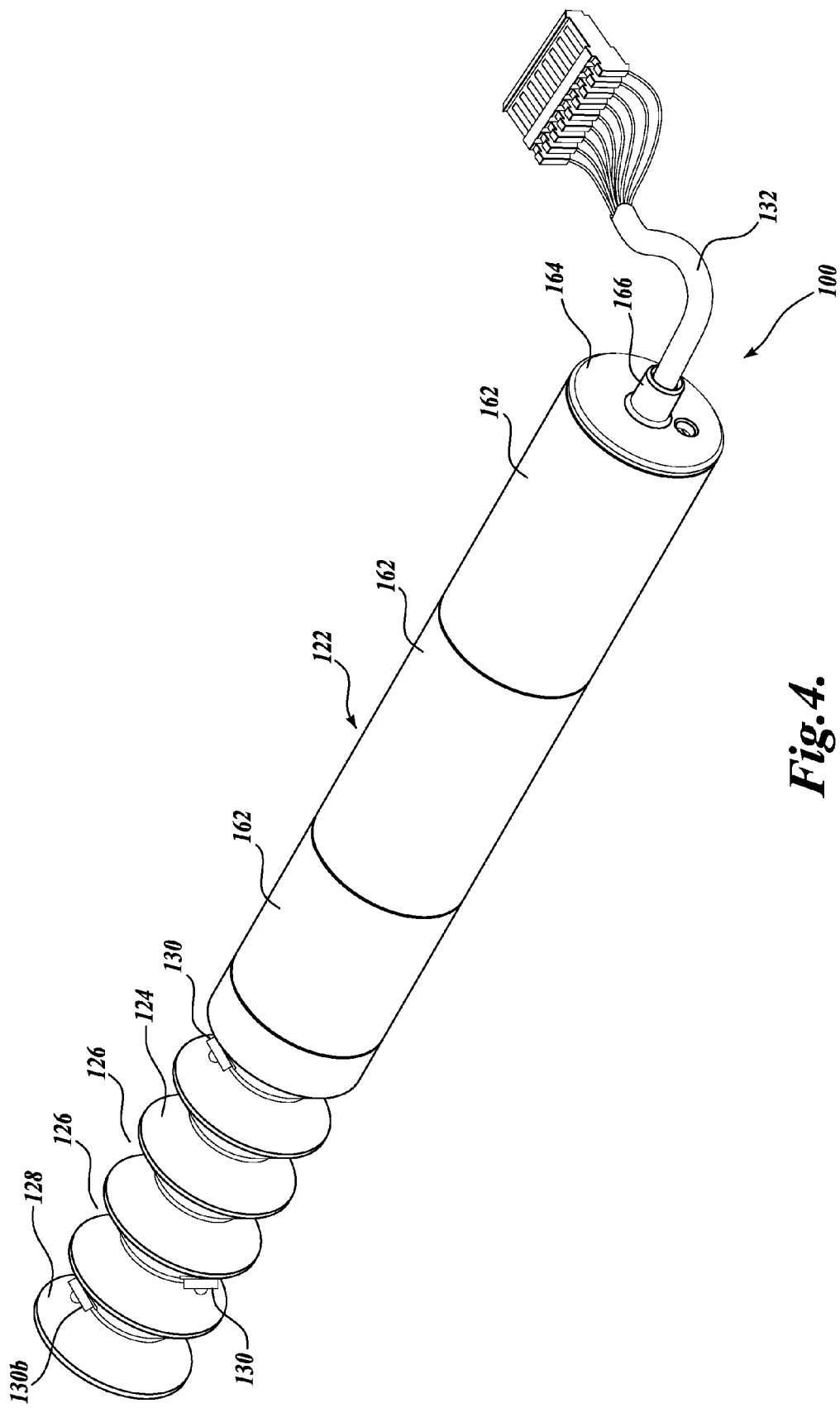
FIG. 4 is a top perspective of a sensor system for liquid detection in accordance with the present invention.
Figure 5:
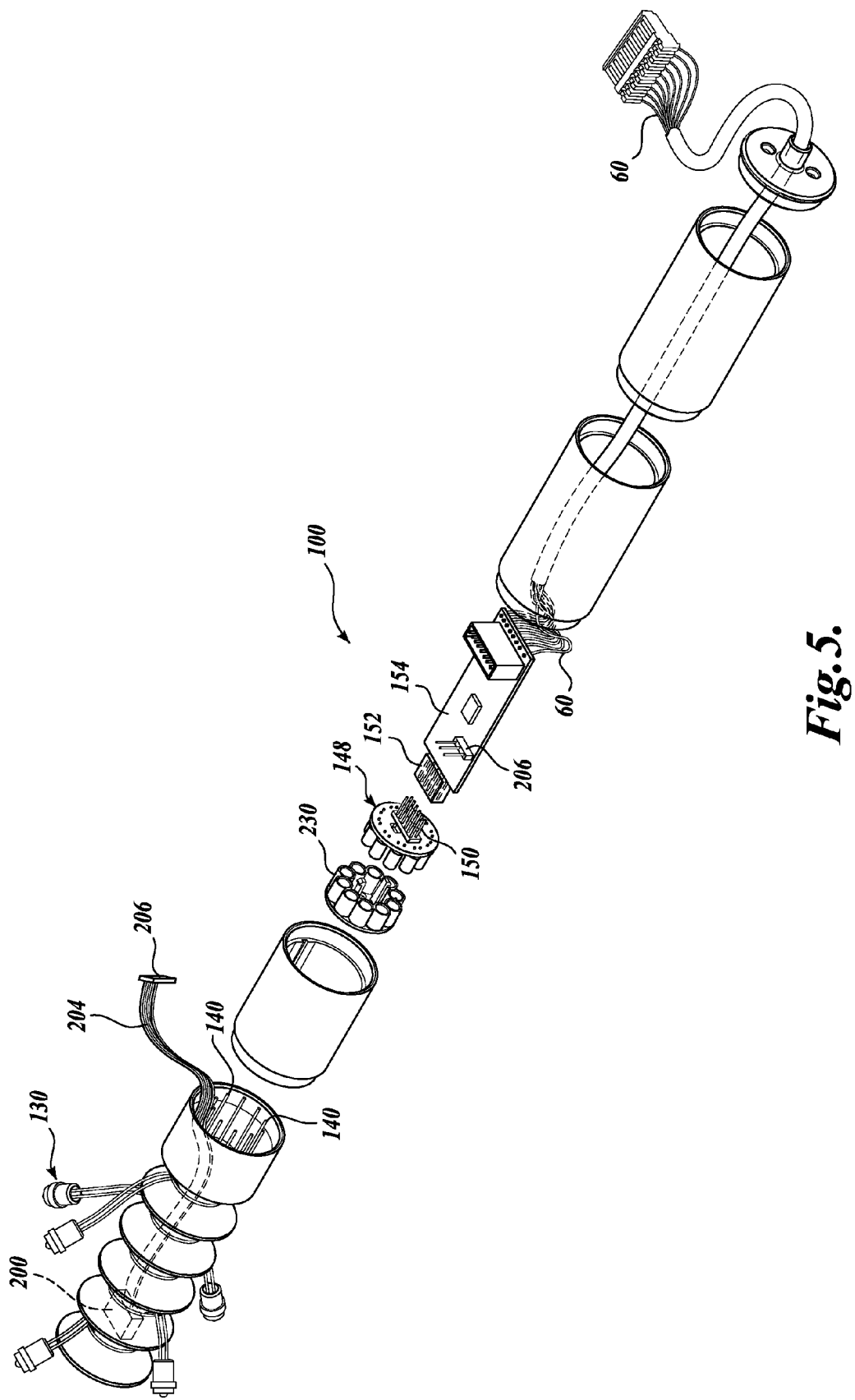
FIG. 5 is a top perspective corresponding to FIG. 4, but with parts shown in exploded relationship.
Figure 6:
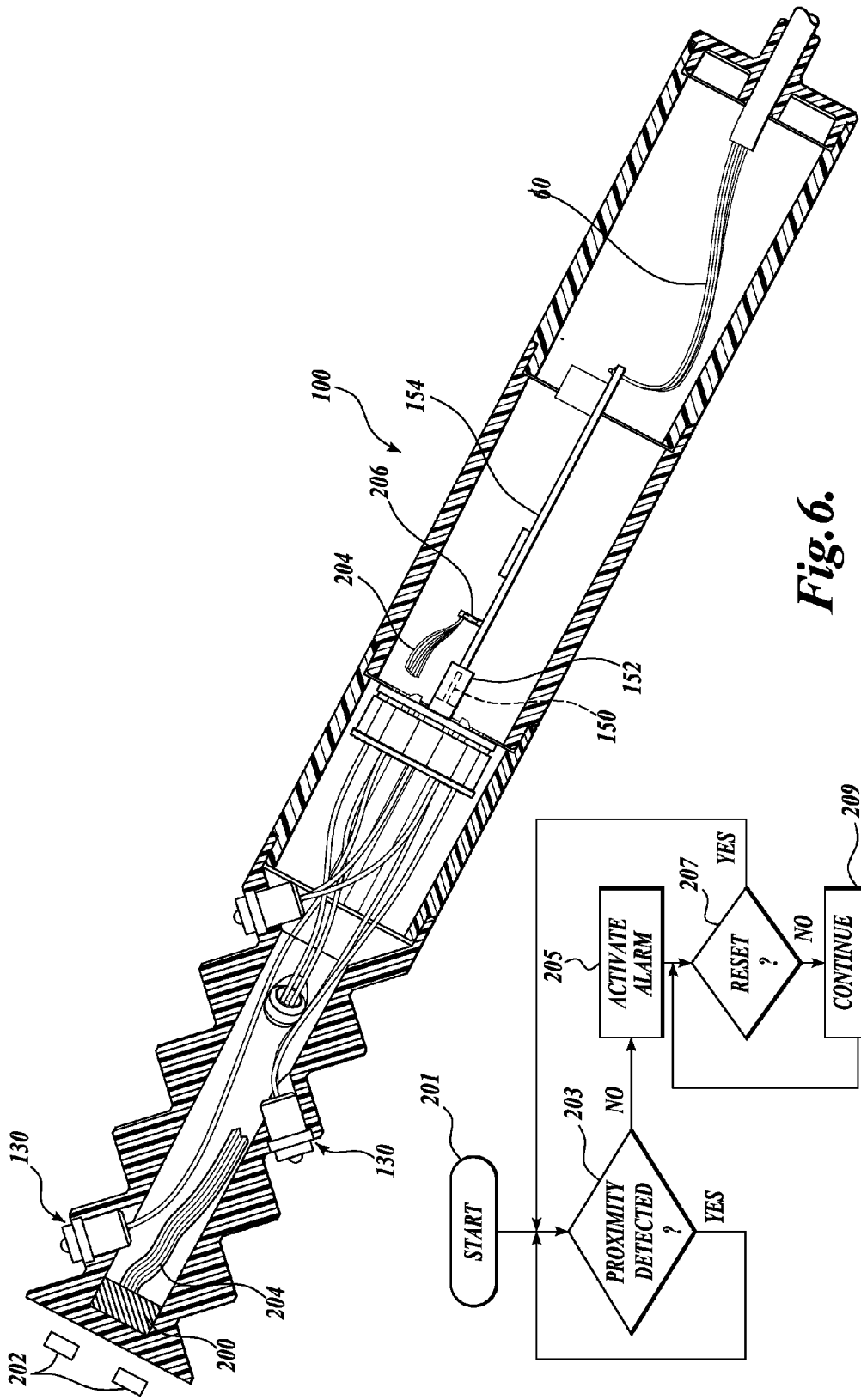
FIG. 6 is a side elevation of the sensor system of FIGS. 4 and 5 with the parts assembled and parts shown in sections.

With reference to FIGS. 4, 5, and 6, the sensor system 100 in accordance with the present invention has components similar to the earlier EOS System, but the later EOS version which is the subject of the present application has several important differences. The cylindrical housing 122 can include separate interfitting shells 162, a bottom or distal end portion 124, and a top or proximate end cap 164 with the central hub 166 for the output cable 132. Individual sensors 130 are mounted in the grooves 126 of the bottom housing portion 124. The foot 128 is much wider than the narrow foot of the earlier design. Foot 128 has a horizontal diameter or extent at least as great as the section of the housing within which the bottom sensor 130b is mounted. Thus, the larger foot 128 acts as a shield that prevents engagement of the bottom sensor against the mounting pipe and/or any other object as the sensor housing is moved longitudinally downward.

As shown diagrammatically in FIGS. 5 and 6, one or more Hall effect sensors 200 are mounted in the foot 128. One or more magnets 202 (shown diagrammatically in FIG. 6) are placed or secured in the bottom of the mounting pipe, such that, when the housing is properly placed at the bottom of the pipe, the Hall effect sensors will detect the presence of the magnets and convey a signal to the microprocessor by way of a wire harness 204 and mating connectors 206. Thus, the microprocessor can receive and supply a signal which will indicate whether or not the Hall effect sensors, once actuated by the magnets, have been moved. Programming of the microprocessor can provide an alarm signal along one of the output wires 60. If desired, once "tripped" by movement from the predetermined operating position, the system alarm may indicate a defect that must be corrected by resetting the microprocessor before the system is again operable. This will prevent tampering going undetected, such as if an individual tries to remove or lift the sensor to avoid signaling a dangerous water-present or fuel-present condition.

FIG. 6A is a diagram of the anti-tamper process. Upon activation of the system (start box 201) a decision is made at 203 as to whether or not the desired proximity condition is detected. In the described embodiment, this is determined by whether or not the Hall effect sensor in the foot detects the presence of the magnets in the bottom of the mounting pipe. If so, the process recycles back to the decision box. If proximity is not detected, indicating that the device has been moved upward away from the bottom of the mounting pipe, an alarm is activated at 205. Next, a decision is made as to whether or not the system has been reset (decision box 207). If it has not, the alarm is continued at 209 and the process recycles to the decision at 207. It is only after reset of the system that the process cycles back to the decision at 203 as to whether or not the device is properly located at the bottom of the tube. It is envisioned that the reset process be sufficiently complicated that a trained technician is required in order to achieve the reset. In that case, tampering with the device will be indicated promptly and continuously, even if the device is moved back to its normal operating position, unless the technician has examined the situation and determined that reactivation of the system is appropriate.

Figure 12:
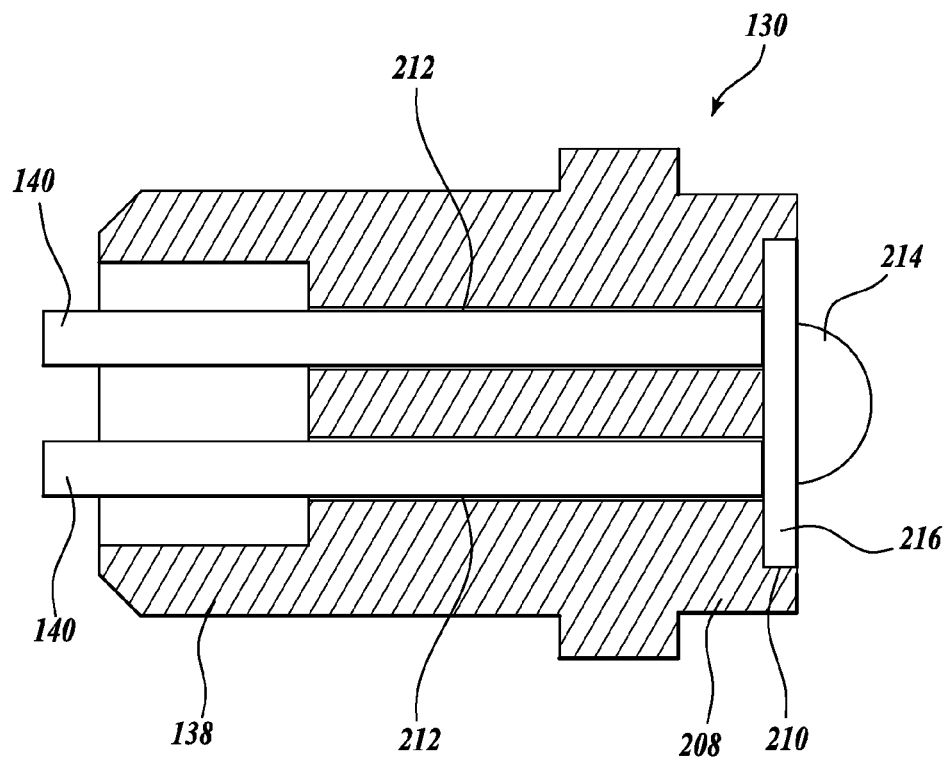
FIG. 12 is a longitudinal axial section thereof.
Figure 13:
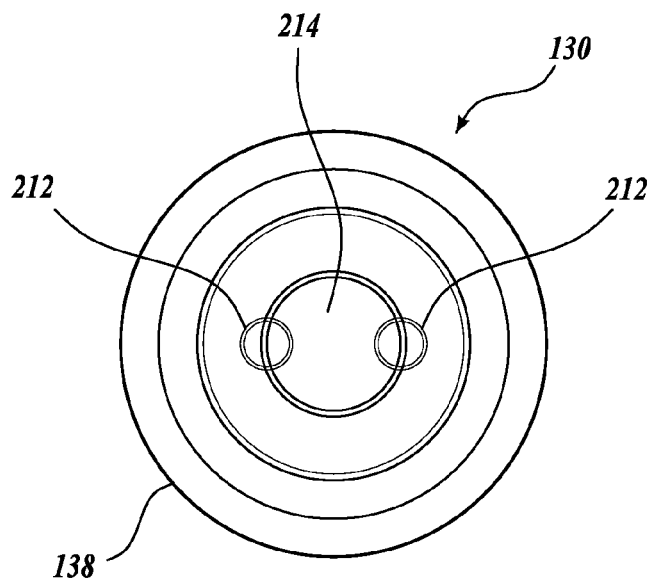
FIG. 13 is a front end elevation thereof.
Figure 14:
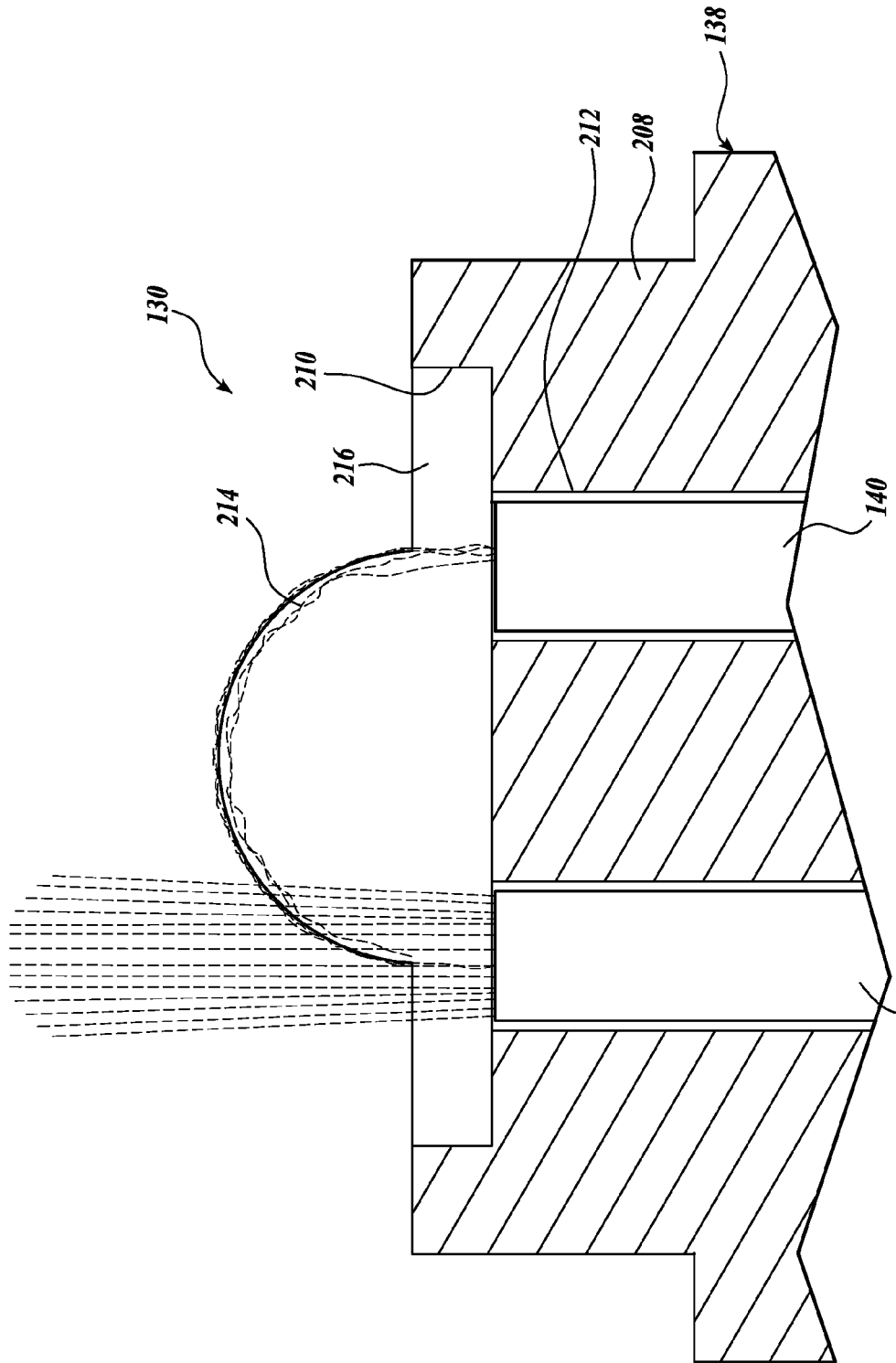
FIG. 14 is a very diagrammatic, enlarged, fragmentary longitudinal section of the distal end portion of a sensor in accordance with the present invention.

The new sensor component 130 is best described with reference to FIGS. 10-14. The modified holder 138 has an exterior shape similar to the holder of the prior art system, including a cylindrical body that fits within the appropriate hole of the housing bottom or distal end, an annular shoulder to limit insertion of the holder into the housing, and an outward projecting cylindrical portion 208 which, at its outer end, has a shallow cylindrical recess or socket 210. The holder can be formed of aluminum. Two holes 212 extend lengthwise through the holder, 180° apart and equidistant from the center. A generally hemispherical lens 214 and a thin, flat, annular base 216 are formed integrally from an optically translucent material, such as clear or nearly clear glass. The lens is approximately a hemisphere with a slight flattening at the apex. In a representative embodiment, the hemisphere base radius can be represented as R and the radius of curvature at the apex nR, where n is a value less than 1.00 but greater than 0.90. Still more specifically, in a representative embodiment, the radius of curvature of the lens at the base is 1.46 mm; the radius of curvature at the apex is 1.43 mm; the thickness of the flat base is 0.25 mm; and the diameter of the base can range from 5.67 mm to 5.92 mm. The diameter of the socket 210 is nearly identical to the diameter of the base 216 so that the lens 214 is precisely positioned in the socket. With reference to FIGS. 12 and 13, the holes 212 also are precisely positioned so that a longitudinal continuation of the edge of the lens (such edge meets the base at an angle of 90° or very close to 90°) will intersect the holes. In a preferred embodiment, the holes are centered at opposite sides of the periphery of the lens such that each hole has a portion projecting beyond the exterior of the lens and a portion projecting inward of the exterior of the lens. Optical fibers 140 are closely received in the holes and secured therein (in a representative embodiment, the diameter of each fiber is approximately 1 mm).

Figure 11:
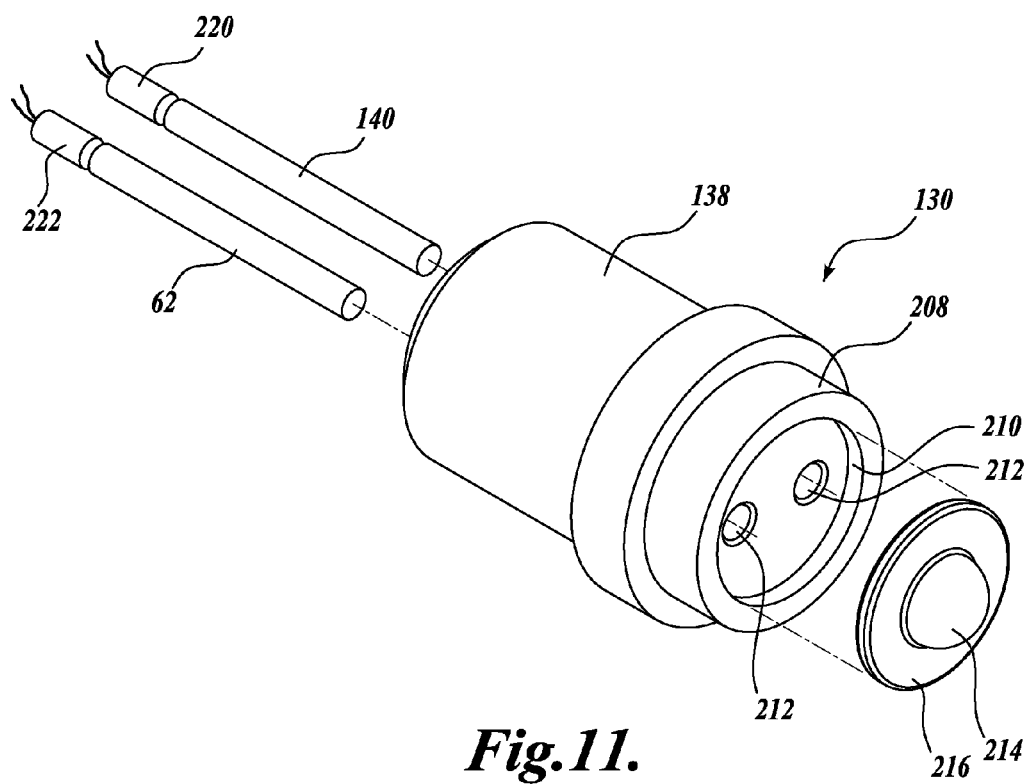
FIG. 11 is a top perspective corresponding to FIG. 10, with parts shown in exploded relationship.
Figure 15:
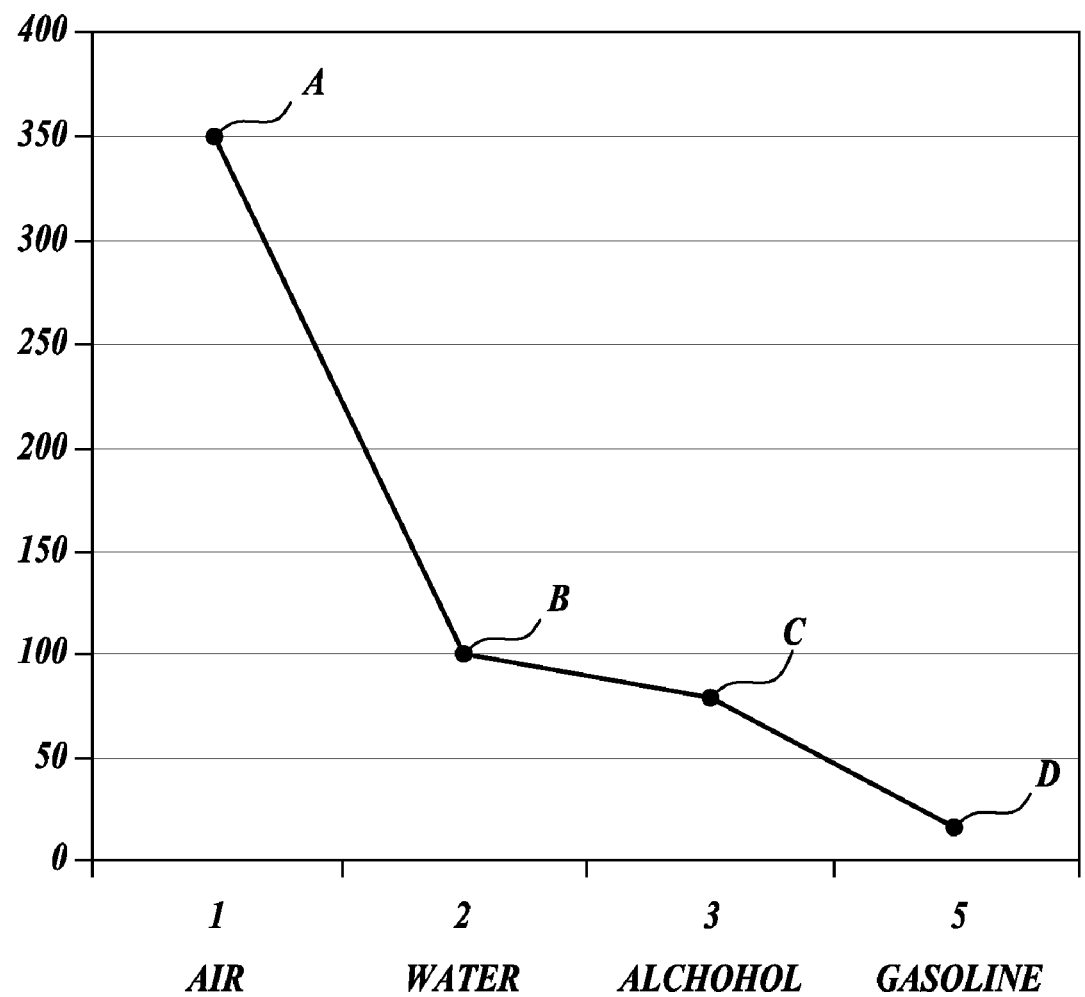
FIG. 15 is a graph illustrating aspects of operation of a sensor in accordance with the present invention.

FIG. 11 illustrates the fibers 140 insertable into the holes 212. From its distal end adjacent to the lens component, one fiber extends to a light source, diagrammatically represented at 220. Infrared light (representative wavelengths of 940-960 nanometers) is transmitted through the fiber 140 by total internal reflection, and out the opposite end, as diagrammatically represented in FIG. 14. Depending on the medium to which the exterior of the lens is exposed, more or less of the light travels along the periphery of the lens, as represented by the broken lines 214 in FIG. 14. The light waves may travel along the exterior lens in an evanescent mode and/or along the interior of the lens in a whispering gallery mode, or due to multiple refractive reflections. In air, a significant portion of the light intensity travels to the opposite side of the lens, then into the other optical fiber 140 and back to a photosensitive component 222 (FIG. 11) such as a photodiode. The photosensitive component provides an output that changes as a function of the intensity detected. For the present invention, FIG. 15 represents the difference in intensity detected depending on whether the medium surrounding the lens is air (high intensity; point A), water (moderate intensity; point B), alcohol (detectably lower intensity; point C), or gasoline (very low intensity; point D). For example, experiments using a sensor system as described above, indicate that light detected by a photodiode at the "output side" of a lens exposed to air has an intensity about 3.5 times that of a lens exposed to water. For alcohol, the intensity is approximately 80% that of water. For gasoline, the detected intensity is much less than one-half the intensity for water. These values are easily convertible to digital values by the microprocessor to indicate the medium to which the lens is exposed.

Known optical sensors rely on refractive losses and do not deliberately use lenses that intersect the cross-section of an optical fiber. In the present invention, it is important that such intersection be provided, i.e., that at least a significant portion, preferably one-half the diameter, of each optical fiber be positioned to the outside of the lens periphery, particularly the light transmitting fiber. Otherwise, the discrimination (contrast) of the output is jeopardized.

Figure 7:
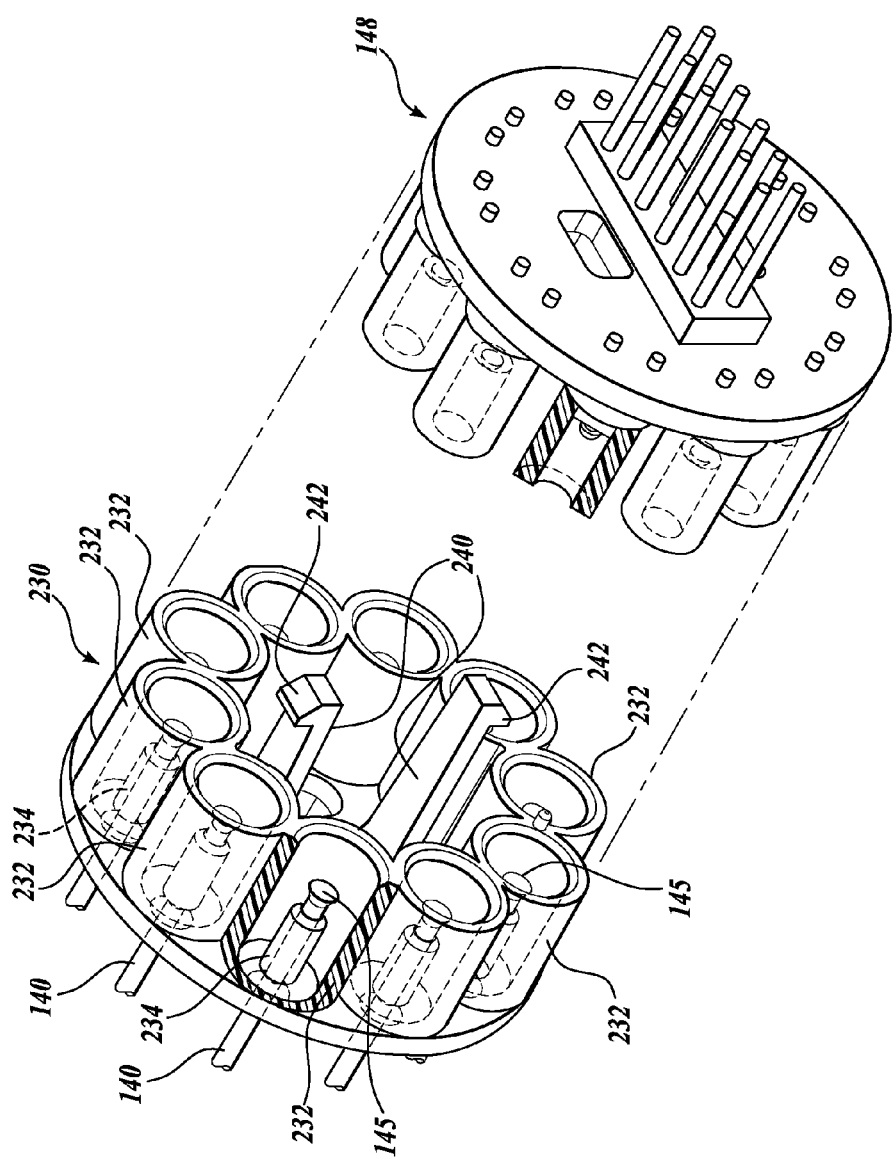
FIG. 7 is an enlarged, somewhat diagrammatic, top perspective of components of the new sensor system in accordance with the present invention.
Figure 9:
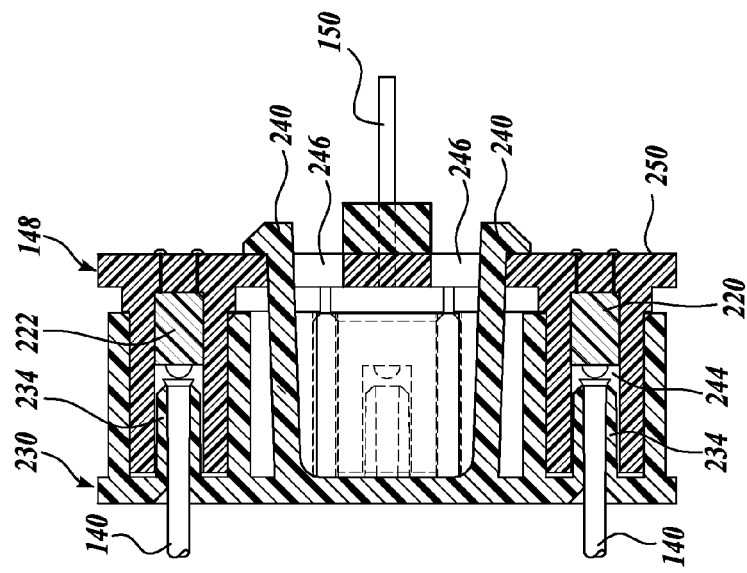
FIG. 9 is a section corresponding to FIG. 8 with parts in different positions.
Figure 8:
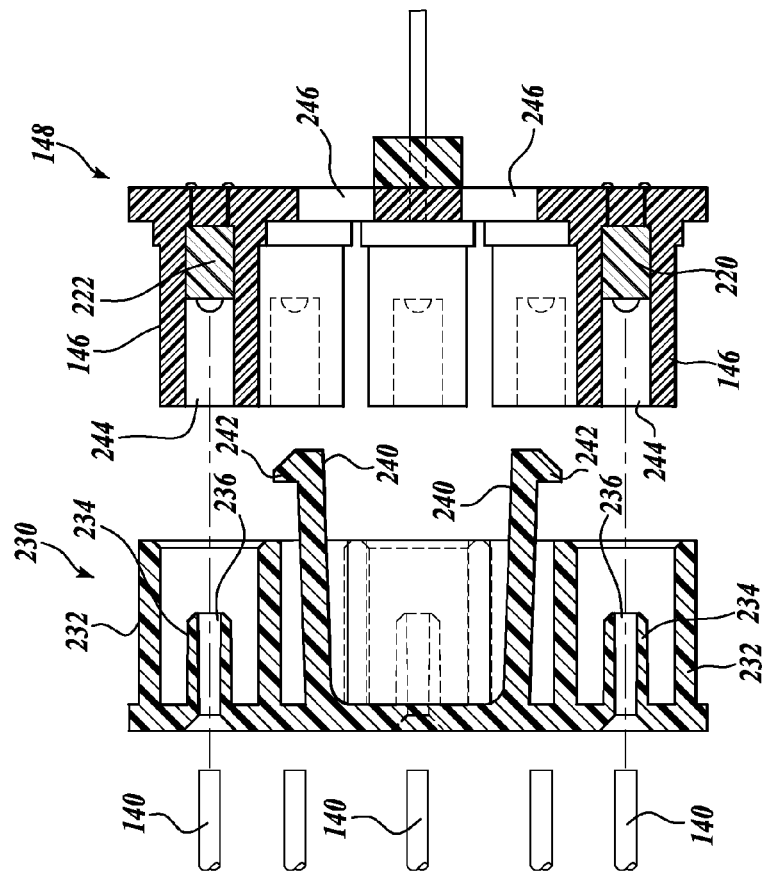
FIG. 8 is a longitudinal section of such components.
Figure 10:
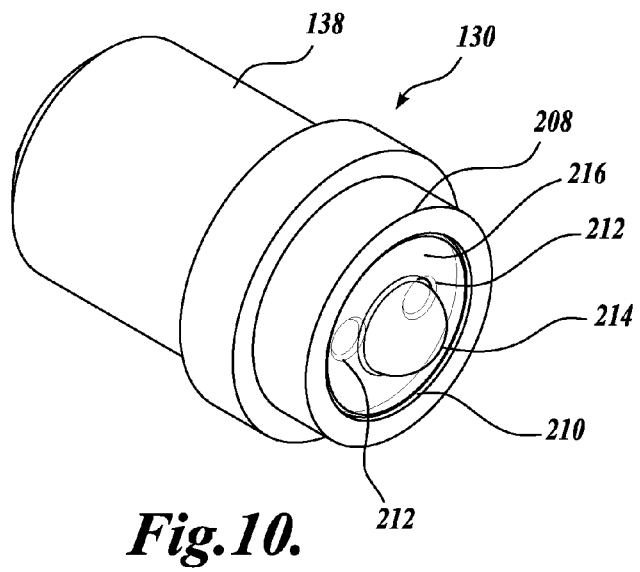
FIG. 10 is a top perspective of parts of an optical sensor in accordance with the invention.

Returning to FIG. 5, the free ends of the optical fibers 140 from the sensors 130 preferably are held in a detangler ring 230. The details of such ring, the fibers received therein, and the connection 148 to which it couples, are best seen in FIGS. 7, 8 and 9. Referring to FIG. 8 (cross-section), the detangler ring 230 has several cylindrical projections 232, one for each of the fibers 140 from the sensors. Within each projection 232, there is a central, integral sleeve 234 having an internal bore 236 almost precisely the same diameter as an optical fiber 140. All of the fibers are inserted through their respective sleeves 234 and severed even with the ends of the other fibers. With reference to FIG. 7, the severing of the fibers results in a slightly enlarged or nonuniform shape (represented at 145) which will not pass back through the sleeve without excessive tension being exerted. Toward the center of the sleeve, two connection prongs 240 project longitudinally in the same direction as the cylindrical projections 232. Prongs 240 extend beyond the projections 232 and have hooked ends 242.

The coupling 148 which mates with the new detangler ring 230 is very similar to the coupling of the prior art embodiment. Alternating light emitting components (light emitting diodes) 220 and photosensitive components (photodiodes) 222 are received in cylindrical protrusions 146 that have cylindrical blind bores 244. As seen in FIG. 9, the detangler ring 230 and coupling 148 can be secured together by aligning the prongs 240 with corresponding openings 246 of the coupling, and chamfers formed on the hooked ends of the prongs result in wedging them together until the hooked ends snap over the outside marginal portions of the openings 246 as seen in FIG. 9. The blind bores 244 snugly receive the sleeves 234 and position the optical fiber ends close to their photo emitting or sensitive elements. The printed circuitry on the back face 250 of the coupling routes to the pins 150 which as seen in FIGS. 5 and 6 mate with the connector 152 from the printed circuit board 154.

In other respects, the sensing system in accordance with the present invention is similar to the prior art EOS sensing system. Separate wires 60 carry signals to and from the microprocessor, including power, ground, water detection, fuel detection, tamper detection (novel to the present invention), as well as binary transmit (TX) and receive (RX) signals for calibrating or reprogramming the microprocessor.

Figure 16:
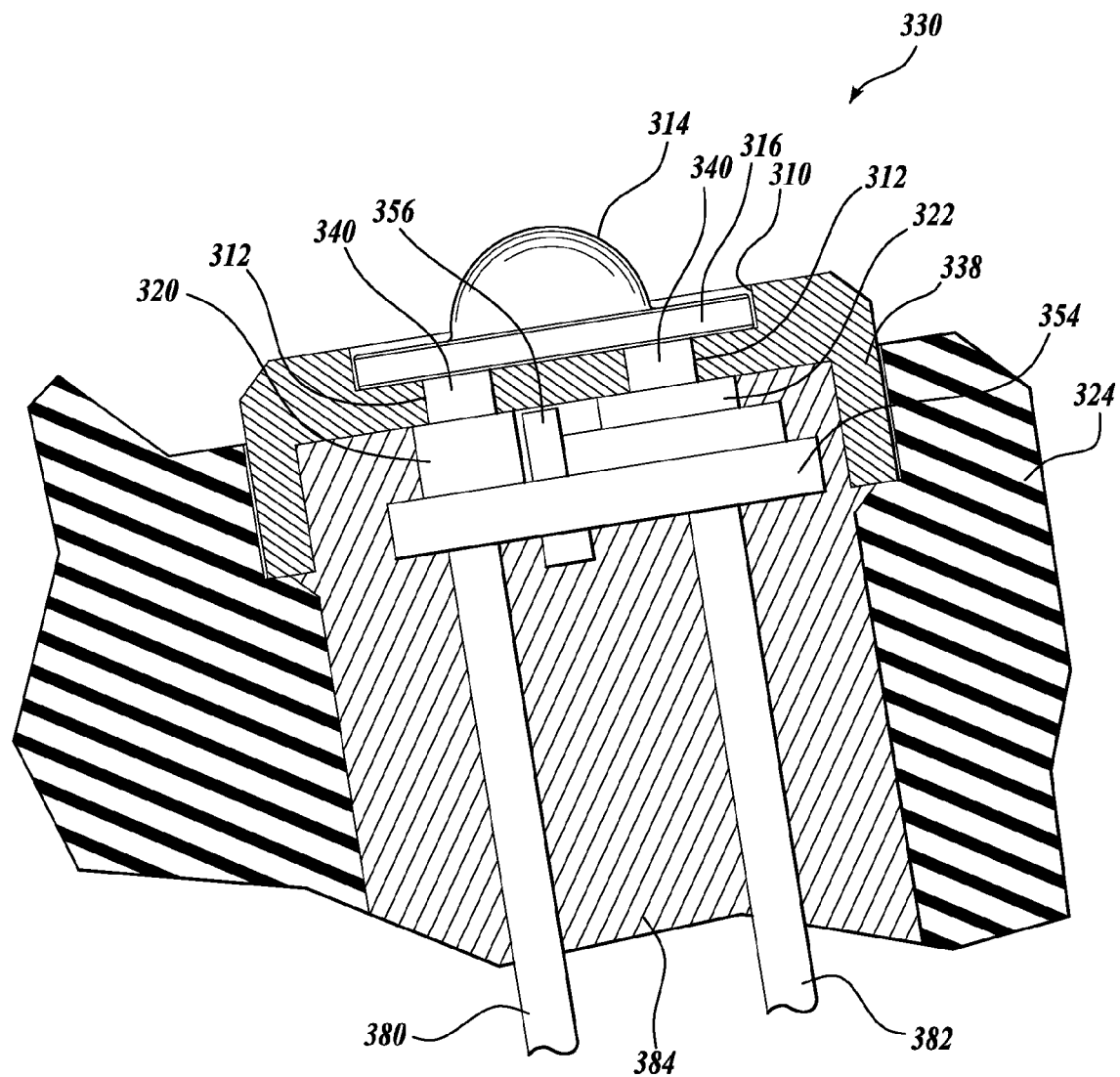
FIG. 16 is a diagrammatic side elevation of another embodiment of a sensor in accordance with the present invention, with parts broken away.

In the embodiment of FIG. 16, the distal end portion 324 of the housing for the individual sensor 330 is the same as previously described. The sensor has a holder 338 with an outward-facing recess or socket 310 of the type previously described. The lens 314 and integral base 316 are identical to the corresponding components previously described, and are mounted in the recess for precise positioning of the lens. The holder has through holes 312 sized and positioned as described for the preceding embodiment.

In the embodiment of FIG. 16, however, the holder 338 is quite short. Holes 312 contain a short segment or stub of optical fiber 340 or other light transmissive material. The light emitting component (LED) 320 is positioned directly adjacent to one of the stubs or sections 340 and the photosensitive component (photodiode) 322 is positioned directly adjacent to the other stub or section. A printed circuit board 354 and microprocessor 356 are positioned close to the holder 338 and carry the photosensitive and photo emitting components. Thus, there are separate photo emitting and photosensitive components, as well as circuit boards and microprocessors for each individual sensor. Power for the sensor can be provided by a wire 380 and output signals supplied along one or more wires 382. The circuitry preferably is potted in a rigid or semi-rigid material 384. Wires 380, 382 can lead to a central circuit and/or microprocessor for evaluation and signaling along a cable similar to the output cable of the embodiment previously described.

Figure 17:
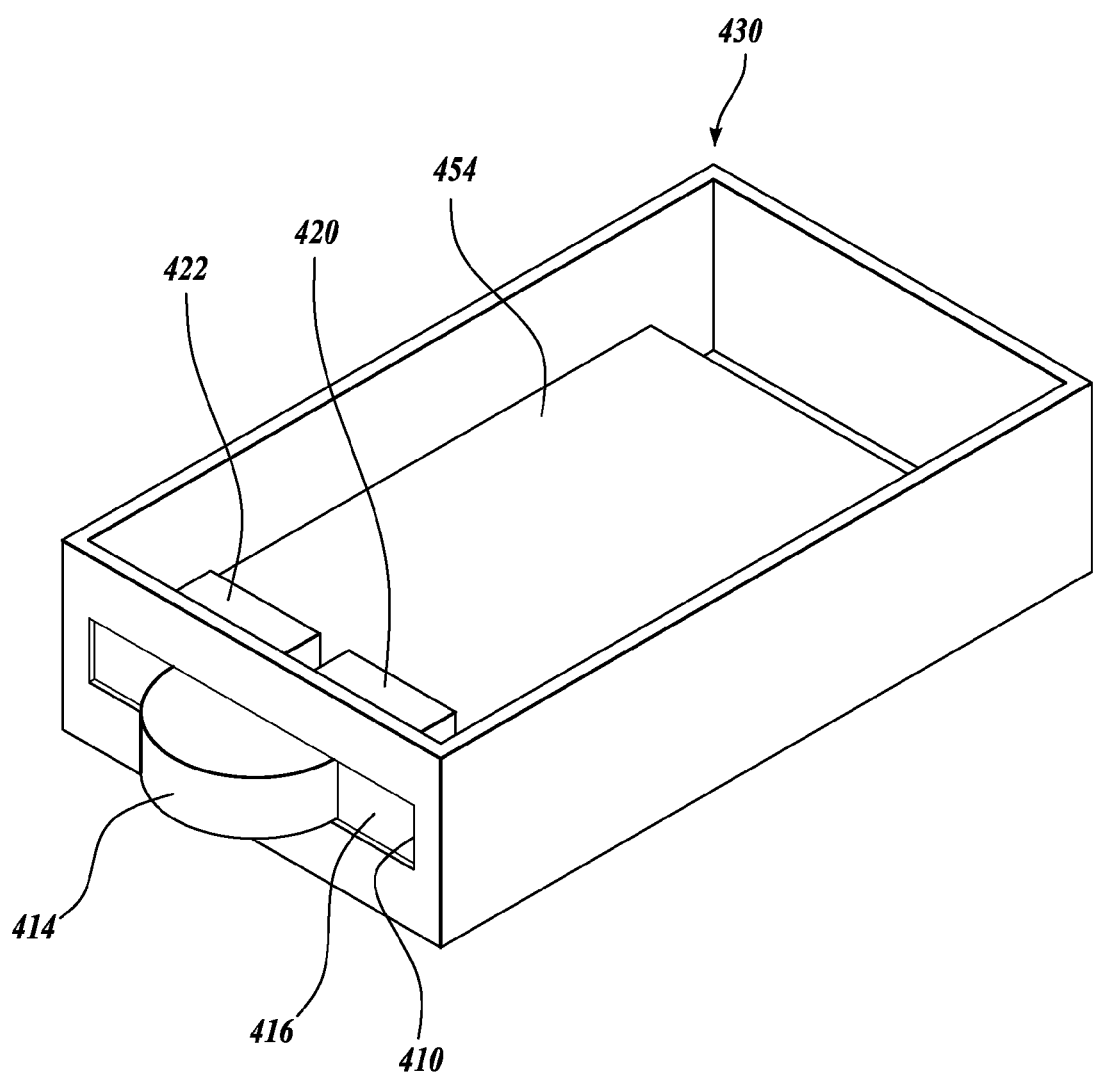
FIG. 17 is a diagrammatic top perspective of component parts of another embodiment of a sensor system in accordance with the present invention.
Figure 18:
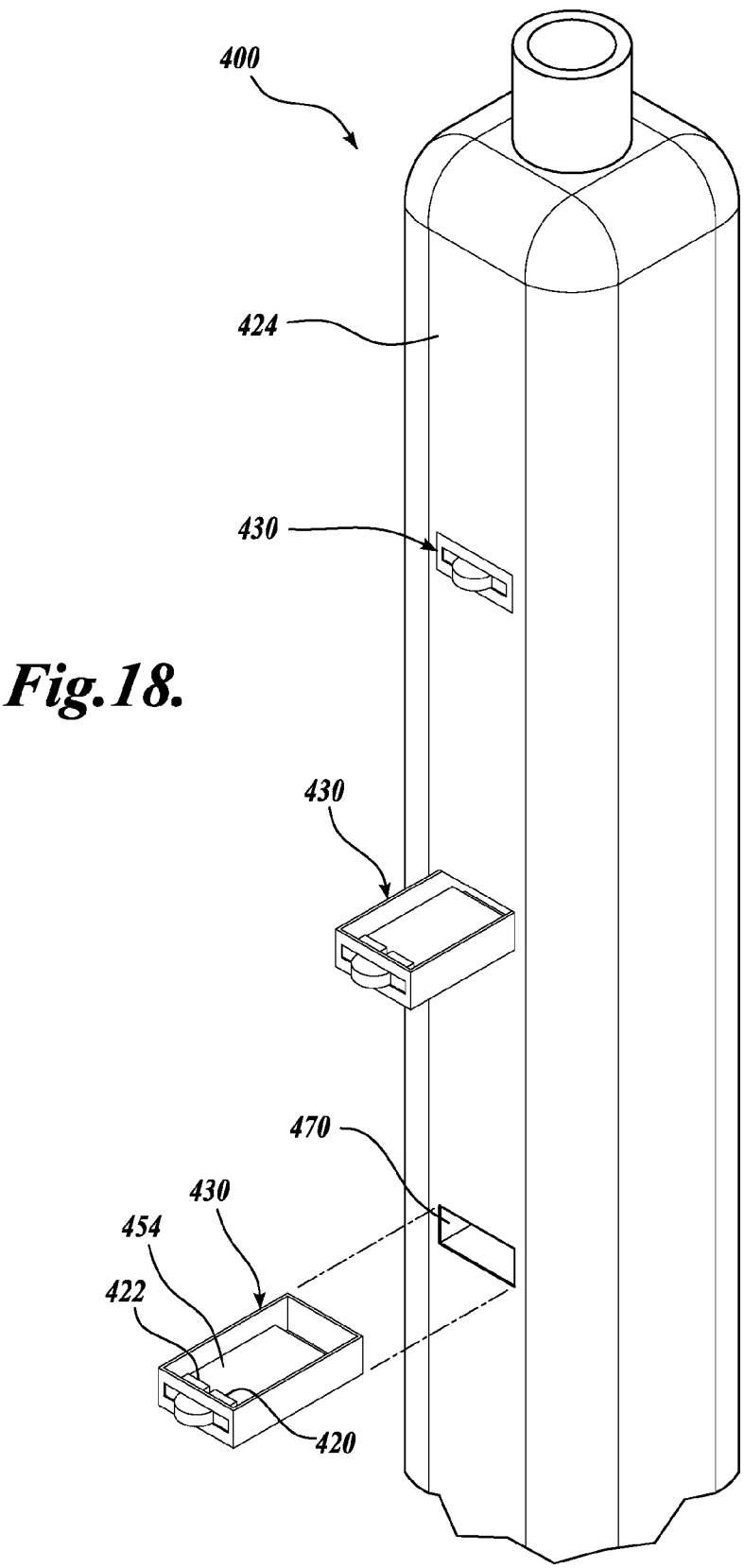
FIG. 18 is a fragmentary top perspective of a multiple sensor system using component parts in accordance with FIG. 17.

FIGS. 17 and 18 diagrammatically illustrate another sensor system 400 similar to the previously described systems. Referring first to FIG. 18, individual sensors 430 are spaced along the length of a housing 424. The housing is hollow, and at least one side has slots or openings 470 for receipt of drawer-like sensor holders 438. Each holder can contain the printed circuit board 454 with microprocessor and output leads, as well as an individual, light emitting component 420 and light sensitive component 422. With reference to FIG. 17, the lens 414 for the embodiment of FIGS. 17 and 18 is a semi-cylindrical shape, preferably formed integral with a thin, flat base 416 resembling tabs or wings extending oppositely from the lens. This configuration is mounted in a recess or socket 410 in the exterior face of the holder 438. The light emitting and light sensitive components are positioned precisely so as to be intersected by a continuation of the opposite sides of the semi-cylindrical lens, which extend at angles of 90°, or close to 90°, to the exterior face of the holder 438. Dimensions for the lens and integral base can be the same as the dimensions for the hemispherical lens and flat base previously described, with respect to radii of curvature, and measured intensity by the light sensitive component is essentially the same as shown in FIG. 15, based on the transmission illustrated diagrammatically in FIG. 14.

While illustrative embodiments have been illustrated and described, it will be appreciated that various changes can be made therein without departing from the spirit and scope of the invention.

The embodiments of the invention in which an exclusive property or privilege is claimed are defined as follows:

1. A sensor assembly comprising:
   a lens component having an apex, an outer periphery with a substantially semi-circular cross-section, and first and second side edge portions disposed at opposite sides of the apex and extending approximately parallel to each other;
   a holder in which the lens component is mounted;
   a light-transmitting component mounted in the holder and transmitting light at the first side edge portion generally toward the apex and generally parallel to the extent of the first side edge portion, the transmitted light including light at the interior of the lens periphery and light at the exterior of the lens periphery;
   a light sensitive component mounted in the holder to detect light emitted at the second side edge portion which light originated at the first side edge portion by virtue of the light-transmitting component.

2. A sensor assembly comprising:
   a lens component having a flat base and an outer periphery with a substantially semi-circular cross-section, the outer periphery of the lens component having an apex and first and second side edge portions disposed at opposite sides of the apex, the first and second side edge portions extending approximately parallel to each other and approximately perpendicular to the flat base, and the first and second side edge portions being connected by a substantially semi-circular cross-section of the outer periphery of the lens component;
   a holder in which the lens component is mounted;
   a light-transmitting component mounted in the holder and transmitting light at the first side edge portion generally toward the apex and generally parallel to the extent of the first side edge portion, the light-transmitting component being mounted in the holder and constructed and arranged to transmit light at the interior of the lens periphery and at the exterior of the lens periphery; and
   a light sensitive component mounted in the holder to detect light emitted at the second side edge portion which light originated at the first side edge portion by virtue of the light-transmitting component.

* * * * *